(12) United States Patent
Phopase

(10) Patent No.: US 10,039,859 B2
(45) Date of Patent: Aug. 7, 2018

(54) TRANSPARENT HYDROGEL AND METHOD OF MAKING THE SAME FROM FUNCTIONALIZED NATURAL POLYMERS

(71) Applicant: UAB Ferentis, Vilnius (LT)

(72) Inventor: Jaywant Phopase, Linkoping (SE)

(73) Assignee: UAB Ferentis, Vilnius (LT)

( * ) Notice: Subject to any disclaimer, the term of this patent is extended or adjusted under 35 U.S.C. 154(b) by 79 days.

(21) Appl. No.: 14/917,193

(22) PCT Filed: Sep. 9, 2014

(86) PCT No.: PCT/EP2014/069205
§ 371 (c)(1),
(2) Date: Mar. 7, 2016

(87) PCT Pub. No.: WO2015/032985
PCT Pub. Date: Mar. 12, 2015

(65) Prior Publication Data
US 2016/0193384 A1    Jul. 7, 2016

(30) Foreign Application Priority Data
Sep. 9, 2013 (SE) ...................... 1351039

(51) Int. Cl.
| A61L 27/24 | (2006.01) |
| A61L 27/22 | (2006.01) |
| A61L 27/26 | (2006.01) |
| A61L 27/34 | (2006.01) |
| A61L 27/48 | (2006.01) |
| A61L 27/52 | (2006.01) |
| A61L 27/18 | (2006.01) |
| A61L 27/38 | (2006.01) |
| A61L 27/54 | (2006.01) |
| A61L 27/58 | (2006.01) |
| C08J 3/24 | (2006.01) |
| C08J 3/075 | (2006.01) |
| C08F 290/06 | (2006.01) |
| C12N 5/00 | (2006.01) |

(52) U.S. Cl.
CPC ............... *A61L 27/24* (2013.01); *A61L 27/18* (2013.01); *A61L 27/227* (2013.01); *A61L 27/26* (2013.01); *A61L 27/34* (2013.01); *A61L 27/38* (2013.01); *A61L 27/48* (2013.01); *A61L 27/52* (2013.01); *A61L 27/54* (2013.01); *A61L 27/58* (2013.01); *C08F 290/065* (2013.01); *C08J 3/075* (2013.01); *C08J 3/243* (2013.01); *C08J 3/246* (2013.01); *C12N 5/0062* (2013.01); *A61L 2300/414* (2013.01); *A61L 2400/18* (2013.01); *A61L 2430/16* (2013.01); *C08J 2333/14* (2013.01); *C08J 2389/00* (2013.01); *C08J 2471/02* (2013.01)

(58) Field of Classification Search
CPC ................ C08F 290/065; C08F 220/20; C08F 2220/286; C08F 283/04; C08F 220/18; C08F 220/28; C08F 222/1006; C08L 89/06; C08L 71/02; A61L 27/26; A61L 27/48; A61L 27/34; A61L 27/24; A61L 27/52; A61L 2430/16; A61L 27/227; A61L 27/50; C12Q 1/687; A61K 48/0033; A61K 48/0066; A61K 9/1271; A61K 48/005; A61K 31/7115; A61K 38/00; A61K 38/17; A61K 38/177; A61K 38/45; A61K 38/193; A61K 38/4846; A61K 38/1816; A61K 38/191; A61K 38/212; A61K 48/0075
See application file for complete search history.

(56) References Cited

U.S. PATENT DOCUMENTS

| 2006/0083773 | A1 | 4/2006 | Myung et al. |
| 2007/0233240 | A1 | 10/2007 | Frank et al. |
| 2008/0287342 | A1 | 11/2008 | Yu et al. |
| 2008/0317818 | A1 | 12/2008 | Griffith et al. |
| 2011/0182968 | A1 | 7/2011 | Myung et al. |
| 2013/0116405 | A1 | 5/2013 | Yu et al. |
| 2014/0142200 | A1 | 5/2014 | Duan et al. |

FOREIGN PATENT DOCUMENTS

| EP | 2535041 A1 | 12/2012 |
| WO | WO-2006042272 A2 | 4/2006 |

OTHER PUBLICATIONS

Myung, David, et al. "Design and fabrication of an artificial cornea based on a photolithographically patterned hydrogel construct." Biomedical Microdevices, Kluwer Academic Publishers, BO, vol. 9, No. 6, Jan. 20, 2007, pp. 911-922, XP019548907, ISSN: 1572-8781, DOI: 10.1007/S10544-006-9040-4.

Liu, Wenguang, et al. "Collagen-phosphorylcholine interpenetrating network hydrogels as corneal substitutes." Biomaterials, Elsevier Science Publishers BV., Barking, GB, vol. 30, No. 8, Mar. 1, 2009, pp. 1551-1559, XP025876351, ISSN: 0142-9612, DOI: 10.1016/Biomaterials.2008.11.022.

International Search Report PCT/ISA/210 for International Application No. PCT/EP2014/069205 dated Nov. 27, 2014.

*Primary Examiner* — Debbie K Ware
(74) *Attorney, Agent, or Firm* — Harness, Dickey & Pierce, P.L.C.

(57) ABSTRACT

The present disclosure relates to a hydrogel derived from a methacrylated or acrylated natural polymer and a synthetic polymer, and a method of preparing the same. The disclosure further relates to 3D scaffolds and implants comprising said hydrogel.

18 Claims, 5 Drawing Sheets

———— MAC    - - - - - - Polymer chain    covalent bond between: ○ MAC-MAC , ● MAC-Polymer

TRANSPARENT HYDROGEL AND METHOD OF MAKING THE SAME FROM FUNCTIONALIZED NATURAL POLYMERS

CROSS-REFERENCE TO RELATED APPLICATIONS

This application is a national phase under 35 U.S.C. § 371 of PCT International Application No. PCT/EP2014/069205 which has an International filing date of Sep. 9, 2014, which claims priority to Swedish Application No. 1351039-1, filed Sep. 9, 2013, the entire contents of each of which are hereby incorporated by reference.

FIELD OF THE INVENTION

The present invention relates to a transparent hydrogel comprising at least one functionalized natural polymer such as collagen or CMP and a method comprising preparing collagen or CMP in order to obtain a transparent hydrogel and cross-linking said collagen or CMP with another polymer via said functional groups. The invention also relates to implants comprising said hydrogel and three-dimensional scaffolds of said hydrogel and cells.

BACKGROUND

Collagen is the most abundant material in the extracellular matrix (ECM) of the human body that surrounds cells and forms the cell-interactive scaffolding of the body. As such, it is completely biocompatible. Hence, it is an excellent biomaterial but has poor mechanical and poor enzymatic stability. In addition, due to limited functionalities (amine and acid) collagen does not provide the flexibility to create a series of multi-functional matrices that are necessary for use as "designer" biomaterials. Therefore, new methodology for modification of collagen with new functional groups, which can lead to diverse chemistry to fabricate covalently linked multi-component biomaterials for regenerative medicine is desirable.

For many tissue engineering and bio-medical applications there is a need for chemically crosslinked collagen materials. A variety of cross-linking procedures are described in the literature. For example to increase its mechanical and enzymatic stability, collagen molecules can be covalently cross-linked leading to the formation of a stable hydrogel. Chemically crosslinked collagen via N-(3-dimethylaminopropyl)-N'-ethylcarbodiimide (EDC) and N-hydroxysuccinimide (NHS) coupling with zero-length crosslinking has been successfully transplanted into humans as an artificial cornea. However, in cases of severe disease condition or microbial attack, where higher secretions of collagenase and matrix metalloproteinase (MMP) enzymes occur, the mechanical stability of collagen-based artificial corneas needs to be enhanced to reduce enzymatic degradation.

Additionally, reproducibility in the preparation of collagen hydrogels via EDC/NHS coupling can be an issue, resulting in batch-to-batch variability. EDC is also highly susceptible to hydrolysis, making this crosslinking procedure unsuitable for dilute collagen concentrations, for instance for encapsulating cells in a collagenous 3-D matrix. Cell encapsulation cannot be carried out with EDC cross-linked collagen due mainly to the smaller pore size of the resulting hydrogel, which (1) impedes nutrient flow to the cells, and (2) squeezes the cells themselves beyond their physiological limit. EDC/NHS coupling reaction also liberates isourea as by-product, which is an established toxic compound.

All the above-mentioned limitations (variations in the hydrogel degree of crosslinking and impossibility in using EDC/NHS coupling for cell encapsulation purposes) constitute an obstacle for its implementation in cornea applications. Different alternatives have already been investigated to improve artificial cornea stability by keeping its fundamental properties constant, like transparency, cell adhesion and hydration. However, there is a general need in enhancing hydrogel mechanical properties in terms of percentage of deformation and elasticity. These issues are further enhanced during suturing of the collagen hydrogels in surgery (cornea transplantations), where brittle hydrogels are an obvious concern.

3D printing is one of the latest "hot" technologies being developed. The most flexible 3D printers extrude "ink" through a syringe positioned and operated by computer-controlled motors, allowing a wide range of materials and stem cells to be used. Biopolymers, hydrogels, and biocompatible polymers are relatively easy to fabricate with this method, but a wide range of other functional materials such as conducting polymers and slurries of hard materials can also be used. Syringe-based printers can be designed with multiple-syringes, or the material in the syringe can be replaced during printing, so that relatively complex assemblies of "living" and otherwise "functional" (for example, electronically-conducting) material can be combined in the same device. 3D printing of organs is a fascinating new area but will still requires the development of appropriate "inks" that are biologically and clinically relevant and that will allow encapsulation of living cells, e.g. stem cells.

Assembly of multiple components that have been pre-fabricated using different methods is yet another method for fabrication of a multi-tissue organ. However, as with 3D printing, there is a need for multicomponent, biointeractive materials.

Even though many hydrogels possess the biocompatibility properties needed they lack in light transmission, i.e. they are not transparent enough.

SUMMARY OF THE INVENTION

Alternative routes to improve robustness of collagen-based implants such as artificial corneas are thus desired. According to the present invention collagen and CMP may be modified to enhance its chemical reactivity towards a range of hydrophilic monomers. The hydrogels of the present invention possess higher mechanical stability and elasticity as compared to the zero-length EDC/NHS crosslinking strategy. Additionally, the hydrogel according to the present invention is also more stable towards enzymatic degradation than pure collagen or hyaluronic acid hydrogels, FIG. 10. The mechanical properties of collagen hydrogels formed in this process are expected to be superior as compared to conventionally prepared collagen hydrogels and the properties may easily be tuned to fit the intended purpose.

The biological response such as tissue regeneration and restoration of functions may also be tailored using the hydrogel according to the present invention by altering for example the composition, cross-linking chemistry and cross-linking density.

Furthermore, hydrogels that act as a 3D matrix to encapsulate stromal stem cells in corneal transplants in cases of patients who have severe damage to their corneas, e.g. chemical burns, are not available. In addition, patients with autoimmune disease can have thinned corneas, and hence, restoration of corneal thickness for both pro-reactive function and vision are desirable. Cell encapsulation for patient-specific applications is a pressing issue that needs to be addressed by formulating 'soft' hydrogels able to engulf stem cells during their polymerization.

Furthermore the present inventors have found that the transparency of collagen based hydrogels can be controlled by manipulating the conductivity of collagen based solutions prior to further modification and/or crosslinking. This is especially interesting when the hydrogel is cross-linked using EDC. The target conductivity is achieved by constant volume diafiltration.

Therefore the aim of the present invention is to present a novel hydrogel comprising at least one natural polymer, for example collagen, and at least one more polymer wherein the chemical and mechanical properties as well as the biological response of the hydrogel may be tailored.

In a first aspect the present invention relates to a hydrogel of a cross-linked polymer network comprising
  at least one first polymer and at least one second polymer wherein the first polymer is a natural polymer provided with methacrylate and/or acrylate functional groups and the second polymer comprises a synthetic and/or a natural polymer having at least two functional groups selected from thiol, acrylate and/or methacrylate;
  wherein the first and the second polymers are cross-linked via said functional groups; and
  wherein the total concentration of polymers in the hydrogel is at least 2 weight %.

In a second aspect the present invention relates to method of preparing the hydrogel comprising:
  providing a solution of a first polymer comprising a natural polymer comprising methacrylate and/or acrylate functional groups;
  providing a second polymer comprising a synthetic and/or a natural polymer having at least two functional groups selected from thiol, acrylate and/or methacrylate, or synthetic and/or natural monomers having thiol, acrylate and/or methacrylate functional groups;
  mixing the first and the second polymer, or monomers, in water to a total polymer concentration of at least 2 weight %; and
  letting the functional groups of the first and the second polymer chains cross-link, optionally applying UV radiation to the mixture when the second polymer has acrylate and/or methacrylate functional groups.

In a third aspect the present invention relates to a three-dimensional scaffold comprising the hydrogel according to the present invention and cells.

In a fourth aspect the present invention relates to an injectable composition comprising a first and a second solution wherein the first solution is an aqueous solution comprising a natural polymer comprising methacrylate and/or acrylate functional groups; and the second solution is an aqueous solution comprising a synthetic and/or a natural polymer having two or more functional groups selected from thiol, acrylate and/or methacrylate functional groups; and wherein the polymer concentration in each solution is at least 5 weight %.

In a fifth aspect the present invention relates to an implant comprising the hydrogel of the present invention.

In a sixth aspect the present invention relates to a lab on a chip comprising the hydrogel according to the present invention.

In a seventh aspect the present invention relates to a method of treating a patient with a damaged or mal functioning cornea comprising replacing the damaged or mal functioning cornea with the implant according to the present invention.

In an eighth aspect the present invention relates to a method of preparing transparent collagen hydrogels comprising
  providing a collagen containing solution having conductivity of 45±5 µS/cm; and
  preparing a collagen hydrogel using said collagen containing solution.

In a ninth aspect the present invention relates to the use of the hydrogel according to the present invention in lab-on-a-chip systems, microscopy and microarray substrates, cell and tissue culture dishes, microwell plates, microfluidic or sampling, separation, purification, analytical tools.

In a tenth aspect the present invention relates to a hydrogel comprising collagen mimetic peptides and cross-linking agents.

DETAILED DESCRIPTION OF THE PRESENT INVENTION

Figure 1:
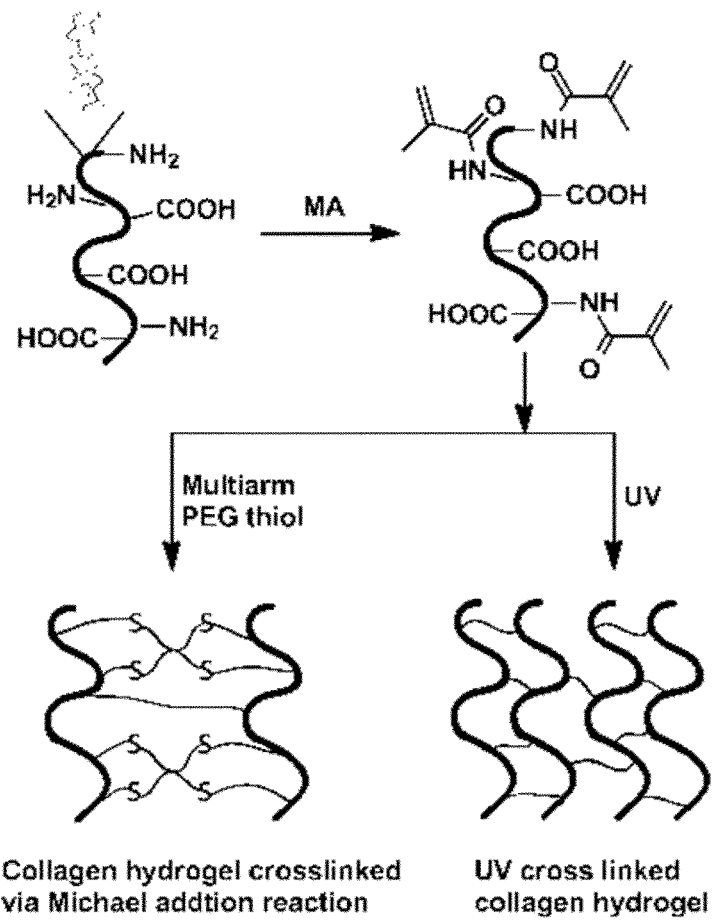
FIG. 1. Collagen methacrylation via addition of methacrylic anhydride (MA), and subsequent crosslinking strategies for hydrogel formation. Examples of (left) Michael addition reaction of 4-arm PEG thiol and (right) UV light irradiation of methacrylated collagen is shown.

In the present invention the term "hydrogel" means a gel of hydrophilic natural or synthetic polymers where the dispersion media is water.

In the present invention the term "arm" means a polymeric chain connected at one common point. For example a two arm polymer has two chains connected at one common point. A star polymer or a star co-polymer is a polymer where several polymeric chains are connected at one common point.

In the present application the term "transparent" means a light transmission of at least 80% of light in a wavelength range of 400-700 nm measured by using any suitably technique for example a UV spectrophotometer, and using pure PBS for background reading.

The Hydrogel

The present invention discloses a hydrogel comprising a first polymer which is a natural polymer, for example collagen or collagen mimetic peptides (CMP), and a second polymer comprising a synthetic and/or natural polymer wherein the second polymer preferably is hydrophilic. Preferably the second polymer is partly or fully water soluble. The first polymer comprises methacrylate and/or acrylate functional groups while the second polymer comprises thiol, methacrylate and/or acrylate functional groups. In one embodiment the hydrogel is cross-linked or further cross-linked using cross-linking agents for example or EDC and NHS. When the hydrogel comprises collagen and/or collagen mimetic peptides (CMP) and cross-linking agents said agents may be EDC and NHS. The molar equivalent ratio of EDC to amine of CMP may be 1:0.5 to 1:3, such as 1:1 to 1:2. The molar ratio of EDC:NHS may be from 2:1 to 1:2, such as 1.5:1 to 1:1.5, or 1:1. By cross-linking the hydrogel via the functional groups (for example methacrylate and thiol) and by the use of EDC:NHS the mechanical properties may be altered and the gelation time may also be shortened.

The first polymer may be selected from collagen, fibrin, cell-interactive proteins (e.g. laminin, fibronectin), hyaluronic acid, chitosan, collagen mimetic peptides, proteins, recombinant proteins or peptides, lignin or cellulose or combinations thereof.

In one embodiment the first polymer is collagen and/or collagen mimetic peptide (CMP). In another embodiment the first polymer is collagen, for example collagen I, collagen II, collagen III, collagen IV or collagen V, or mixtures thereof.

The second polymer may comprise one or more of PEG, PVA, polyethylene glycol-diacrylate (PEGDA), PEG methacrylate (PEGMA), poly(hydroxyethyl methacrylate) (pHEMA), polyethylene glycol methyl ether methacrylate (PEGMEM), poly(pentaerythritol triacrylate), PNIPAAm, silk, collagen, hyaluronic acid, chitosan, collagen mimetic peptides, chimeric peptides based on collagen and cell-interactive peptides, plant lignin, cellulose or plant gum proteins, recombinant proteins or peptides, and co-polymers thereof.

In one embodiment the second polymer is a synthetic polymer, preferably selected from one or more of polyethylene glycol (PEG), polyvinyl alcohol (PVA), polyethylene glycol-diacrylate (PEGDA), PEG methacrylate (PEGMA), poly(hydroxyethyl methacrylate) (pHEMA), polyethylene glycol methyl ether methacrylate (PEGMEM), poly(pentaerythritol triacrylate) or poly(N-isopropylacryl amide) (PNIPAAm). The cell-interactive peptides may be laminin, fibronectin, entactin or vitronectin. In one embodiment the second polymer comprises at least two arms, preferably three or more arms, or four or more arms.

In one embodiment the hydrogel comprises one additional second polymer selected from polyethylene glycol (PEG), polyvinyl alcohol (PVA), polyethylene glycol-diacrylate (PEGDA), PEG methacrylate (PEGMA), poly(hydroxyethyl methacrylate) (pHEMA), polyethylene glycol methyl ether methacrylate (PEGMEM), poly(pentaerythritol triacrylate) or poly(N-isopropylacryl amide) (PNIPAAm). The molar ratio between the second polymer and the additional second polymer may be 3:1 to 0.5:1, such as 2:1 to 1:1.

In one embodiment the second polymer is PEG with 2, 4 or 6 arms. In one embodiment the second polymer or the additional second polymer is PEG with four arms with thiol groups.

The mechanical properties of the hydrogels can be tuned by varying the methacrylated/acrylated collagen or CMP concentration and/or the methacrylated/acrylated collagen/CMP:thiol molar ratio (or acrylate or methacrylate ratio), thus controlling the degree of crosslinking. Soft hydrogels will be produced with initial collagen/CMP concentrations of 3 and 5 wt %. The collagen/CMP:thiol molar ratio (or acrylate or methacrylate ratio) may be varied from 1 to 10, such as 2 to 8, or 3 to 6. The molar ratio between the functional groups of the first polymer and the functional groups of the second polymer may be from 1:5 to 1:0.5 such as 1:3 to 1:1, or 1:2. Cell viability and proliferation will be assessed on the resulting hydrogels in order to understand the optimal hydrogel mechanical properties that favour cell survival and ultimately regeneration.

Figure 9:
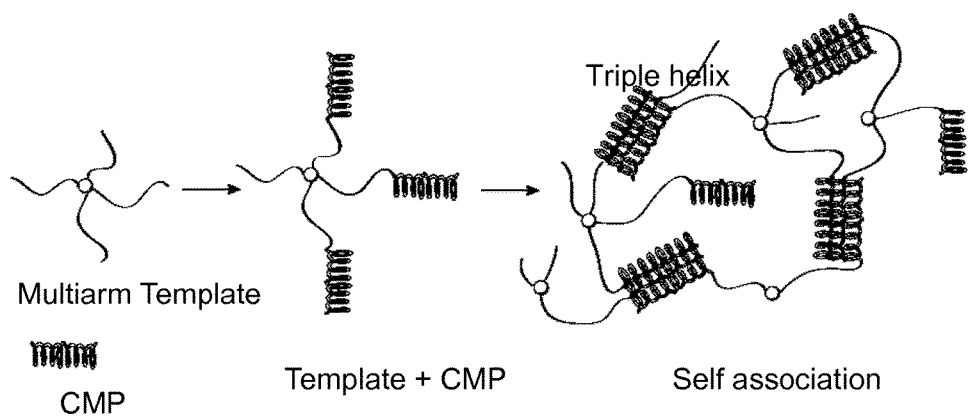
FIG. 9. Schematic figure of preparation of template assisted triple helical polypeptides.

Collagen mimetic peptides (CMP) are short synthetic peptides (15-100 amino acids long, preferably 20-40 amino acids) with an inherent ability to adopt a triple helical fold similar to the natural collagen. CMP's have mainly been used as model systems for elucidating and understanding the formation and stability of triple helix in the natural collagens. In order to enhance CMP's ability to form nanofibers and hydrogels CMP may be connected to a template. Without being bound by theory the template may stabilize the triple helix of the CMP and thereby enhance the possible formation of higher order of assembly. The template may be a polymer or a co-polymer and may have at least two arms (such as 3, 4, 5 or 6 arms) or the templates may be a multiple branched molecule or polymer such as spider silk, hyperbranched polymers or dendrimers. In one embodiment the template is multiarm polyvinylchloride. In another embodiment the template may be a succinylated poly(N-isoacrylamide), e.g. terpolymer of poly(N-isopropylacrylamide-coacrylic acid-coacryloxysuccinimide or PNiPAAm-coAAc-coASI. Preferably the template has two or more long chains, for example each chain may have a molecular weight of at least 5000 g/mol, or at least 15,000 g/mol. The arms or branches of the template comprise functional groups that may form secondary bonds such as hydrogen bonds or dipole-dipole bonds. FIG. 9 discloses CMP and templates and the formation of triple helix.

The present inventors have found that they may produce collagen or CMP hydrogels that are transparent (for example the light transmission may be at least 80%, or at least 85%, or preferably at least 90% for wave lengths between 400 and 700 nm, and with backscatter under 3%, as low as 1%). This is very interesting in certain applications such as intraocular lenses, cornea implants or prosthesis etc., and also when the hydrogels are cross-linked with EDC.

The hydrogels of the present invention are cross-linked via the functional groups of the first and the second polymer and optionally via cross-linking agents. In one embodiment the cross-link is a thio-ether as a result of a reaction between a methacrylate and a thiol group. In another embodiment the cross-link is a carbon-carbon bond for example as a result from a reaction between methacrylate or acrylate groups.

Method of Forming the Hydrogel

The hydrogels may be prepared by mixing a first and a second polymer or by mixing a first and a second solution where the first solution comprises the first polymer and the second solution comprises the second polymer. In one embodiment the pH of the first solution is less than 5, preferably less than 3, or more than 10, preferably more than 12. The first and the second solution may be prepared using water or purified water or any suitable buffer. In one embodiment the first polymer is methacrylated collagen or methacrylated CMP, and wherein the pH of the first solution is less than 5 or more than 10.

Without being bound by theory it is believed that the introduction of photochemically cross-linkable moieties into the first natural polymer will facilitate rapid and controllable intermolecular and intramolecular cross-linking leading to formation of a hydrogel. The cross-linking reactivity of the first natural polymer is enhanced by the incorporation of methacrylate and/or acrylate groups along its triple helical chain, which render it reactive towards nucleophilic attacks via Michael addition reaction. In addition, by being susceptible of radical formation under low-energy UV light irradiation, methacrylate groups offer another synthetic route to bridge collagen helices with a series of hydrophilic compounds (non-zero crosslinking). This modification makes the method presented herein very versatile for the synthesis of collagen/CMP-based hydrogels. The method according to the present invention may use UV in order to form cross-links or to speed up the cross-linking formation, for example UV 365 nm wavelength may be used for 5 to 15 min. In one embodiment a photoinitiator is used, for example at a concentration of 1-5% (w.r.t. to the first polymer). However, the method of preparing the present hydrogels does not require the use of UV, in one embodiment no UV is used.

When preparing the hydrogel the collagen or CMP concentration in the first solution may be 0.2 weight % or higher, or 0.5 weight % or higher, or 1 weight % or higher, or 2 weight % or higher, 5 weight % or higher, or 8 weight % or higher, or 12 weight % or higher, or 15 weight % or higher, up to 18 weight %.

When the hydrogel according to the present invention is prepared using CMP and a template the molar ratio between CMP and the template may be 10:1 to 1:10, such as 5:1 to 1:5, or 2:1 to 1:2.

The hydrogels may be prepared using a syringe mixing system. In a non-limiting example, a collagen (a first polymer) solution is placed into a syringe coupled to a second empty syringe through a 3-way T connector with septum at one end. Solutions of monomers/polymers (a second polymer/monomer) and photo initiator are then added sequentially from syringes via septum and mixed by pumping the combined solutions between the two main syringes. In one embodiment the injectable composition comprises a first and a second aqueous solution wherein the first solution is an aqueous solution comprising collagen or collagen mimetic peptide (CMP) comprising methacrylate and/or acrylate. The second solution is an aqueous solution comprising a synthetic polymer having two or more functional groups selected from thiol, acrylate and/or methacrylate functional groups. The polymer concentration in each solution is not more than 3 weight % in order to facilitate proper mixing and not too high viscosity. In one embodiment the composition further comprises cells and/or growth factors and/or cell nutrients.

The hydrogel may be prepared using a syringe mixing system. The syringe mixing system allows for a coupling reaction mostly in the localized regions where a concentrated aqueous collagen or CMP solution comes into contact with the crosslinking agents. In yet another embodiment the composition is arranged in a syringe wherein the first solution is arranged in a first compartment and the second solution in a second compartment.

The functionalizations of the natural and synthetic polymers and the system for forming hydrogels presented herein are also suitable as inks for 3D printing in order to prepare complex 3D structures, or for incorporating cells into the structure for example. The hydrogels of the present invention may be prepared together with cells, for example stem cells.

Amending the Conductivity of a Collagen Solution

The present inventors have found that the transparency of collagen based hydrogels can be controlled by manipulating the conductivity of collagen based solutions prior to further modification and/or crosslinking. The target conductivity is achieved by constant volume diafiltration.

In a non-limiting example a diafiltration system and membrane of choice is set-up as per the manufacturer's directions. A conductivity sensor is inserted into the permeate line as close as possible to the permeate exit port and the conductivity sensor is connected to a digital recording device. The collagen based solution is diafiltrated at constant volume using water (preferably sterile), USP (e.g. WFI) until the target conductivity is achieved. The processing data (permeate conductivity and temperature) are recorded every 60 seconds. The conductivity for each diavolume of permeate is noted.

For many collagen-based solutions and crosslinking methods the target conductivity to achieve hydrogels with optimized transparency has been found to be 45±5 µS/cm or 45±2 µS/cm. The target conductivity may be adjusted as required for alternative modifications and crosslinking methods.

The present method is applicable to all starting volumes of collagen based solutions. Ten to twenty diavolumes of water (preferably purified such as sterile for example USP water) is consumed to reach the above stated target conductivity. The temperature of the collagen solution throughout the process is preferably kept within 4 to 30° C., or 10 to 25° C., and must be controlled in a manner such that the temperature of the permeate passing thru the conductivity sensor is kept constant (±1° C., preferably ±0.5° C.) and within the calibration range (±1° C., preferably ±0.5° C.) of the sensor. The present inventors have found that if the temperature is not kept constant the correct conductivity of the solution will not be detected. The feed flow rate and feed pressure is dependent upon the diafiltration system used and may be adjusted in accordance with common practice. The present inventors have found that one feed flow rate that may be used is 1-10 LPM/m$^2$ (LPM means liters per minute), or 2-7 LPM/m$^2$, or 3-5 LPM/m$^2$ and a maximum feed pressure may be 10-35 PSI (69-241 kPa), or 15-30 PSI (103-207 kPa), or 20-25 PSI (138-172 kPa) or 25 PSI (172 kPa). The feed flow rate and feed pressure is preferably controlled in a manner that ensures a sufficient permeate flow rate thru the conductivity sensor. The present inventors have found that diafiltration time for 1 liter of a collagen based solution may be 8 to 10 hours. In one embodiment the diafiltrated solution is lyophilized followed by reconstitution of the collagen, i.e. making a new solution at any suitable concentration of the lyophilized collagen or CMP using water or any suitable buffer solution.

Light transmission and back-scattering measurements may be carried out at room temperature for white light (quartz-halogen lamp source) and for narrow spectral regions (centered at 450, 500, 550, 600 and 650 nm). In one embodiment a custom-built instrument was used to measure the percent transmission of samples as compared to open beam intensity. The relative percent of light back scattered from the collimated beam by the sample was measured with a circular array of 8 photodiodes, 30 degrees off axis.

Synthesis of Collagen-Containing Hydrogels Via Thiol-ene Chemistry

Methacrylation and/or acrylation of collagen and/or CMP for example will pave the way to diverse chemical cross-linking strategies, such as Michael addition reaction of nucleophilic functionalities, thiol-ene chemistry and UV irradiation. In addition, bio-active moieties, such as RGD, YIGSR, and IKVAV, can be easily mobilized to MAC (methacrylated collagen) via cysteine thiol residues introduced as end group. The absence of methacrylated sites on unmodified collagen has so far hindered the direct covalent linkage of such bioactive peptides, allowing only for their random physical inclusion. The methacrylation or acrylation of collagen or CMP opens up new synthetic routes towards a variety of modifications.

FIG. 1. The robust nature of thiol-ene chemistry has unique advantages as compared to traditional coupling strategies. Covalent crosslinking of multi-arm PEG thiol to MA-Collagen occurred via direct Michael addition reaction of thiol functionalities to methacrylic groups in collagen. The hydrophilicity of PEG will generate a water-swollen gel that mimics the high water content of the ECM and simultaneously reduce nonspecific protein adsorption and cell adhesion. Furthermore, PEG conjugation reactions are well-understood, allowing biofunctionalities to be easily incorporated into PEG-based hydrogels to spur cell activity. It is important to point out that the addition of thiols to a methacrylic group (thiol-ene chemistry) occurs overnight without the need for either UV radiation or crosslinkers. Thus, Irgacure or APS/TEMED are not needed in this type of coupling reactions. Hydrogels with enhanced mechanical properties will be synthesized with concentrated collagen solutions (from 10 to 20 wt %). 4-armed PEGs may be substituted with a range of other macromolecules including synthetic GAGs, other peptides (X-shaped laminin), recombinant silk, elastin and so on.

Hydrogels from Methacrylated Collagen (MAC) and a Second Compound

MAC-pHEMA

MAC forms a hydrogel under low-energy UV-A light irradiation (365 nm, 4 mW/cm$^2$) via crosslinking of its methacrylated residues. Likewise, HEMA will polymerize forming pHEMA chains. The co-polymerization of MAC and pHEMA will lead to covalently cross linked hydrogels. Other concurrent reactions will involve MAC/MAC and MAC/pHEMA crosslinking.

MAC-Triacrylated Polymer

Figure 2:
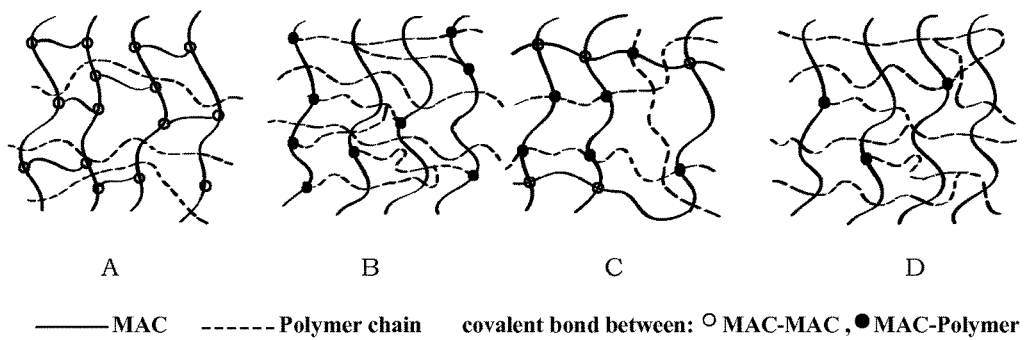
FIG. 2. (A) IPNs with MAC-MAC cross-linked while the other component (polymer) is embedded in the MAC network without cross linking with MAC. (B) IPNs with MAC-Polymer cross-linked and polymer embedded in the network without cross linking. (C) IPNs with MAC-MAC cross linked and MAC-Polymer cross linked. (D) Polymer attached to MAC at one end while remaining two polymer branches forming IPN without cross linking to MAC FIG. 3. A schematic figure of how to build a skin model. The dermal layer may be engineered by plastic compressed and/or electrospun reinforced collagen/fibrin containing endothelial cells/fibroblasts and/or growth factor reservoirs and additionally it may be engineered with channels by 3D printing.
Figure 3:
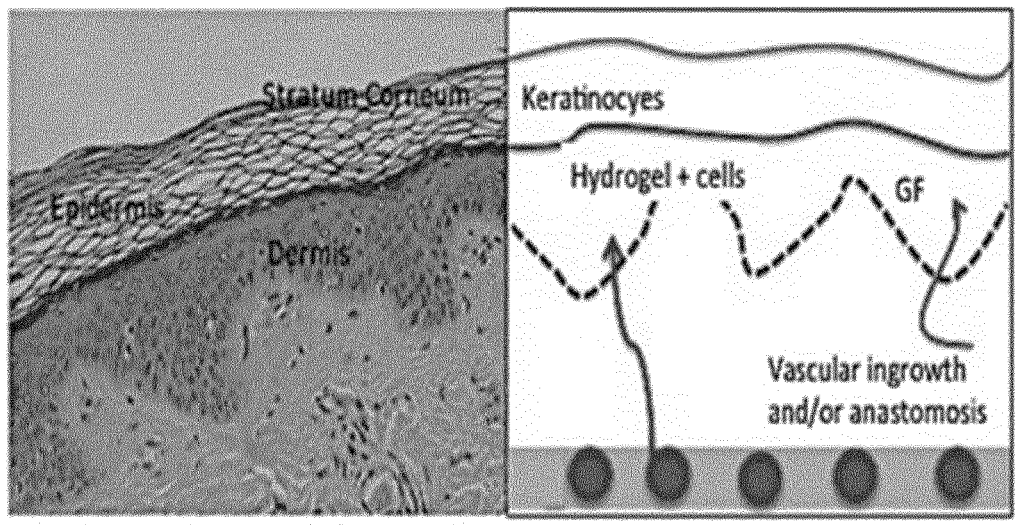

MAC forms a hydrogel under low-energy UV irradiation (365 nm, 4 mW/cm$^2$) via crosslinking of its methacrylated residues. Likewise, pentaerythritol triacrylate will polymerize forming branched polymer chains. The co-polymerization of MAC and triacrylate will lead to hydrogel comprising mixture of different networks. A schematic of composite hydrogel comprising different possible assemblies is depicted in FIG. 2.

The resulting hydrogel will be mixture of all the networks depicted above and complexity of such composite material will increase with increasing number of methyacrylate groups and number of components.

It should be noted that traditional hydrogels only consist of type A while the hydrogels created by the present method will lead to a hydrogel comprising all above (A, B and C) types.

Furthermore, biomaterials consisting only of type A most often, after implantation into animals, lose their bioactive properties due to the degradation of natural bioactive component. In our multi component covalently cross linked material the degradation rate (including mechanical strength) of the bioactive component will be decreased significantly since it is covalently linked to the synthetic polymers (which usually is inert to enzymatic degradation)

It will also provide us the ability to tailor the properties of material (mechanical strength, pore size, elasticity etc) either by varying the components and their ratios.

Applications

The present invention may be used as an implant itself or as part of an implant or as a vehicle for delivering active compounds such as drugs or growth factors for example. A non-limiting list of potential implants is intraocular lenses, cornea, breast, lips, skin, or cardiac patches.

Figure 4:
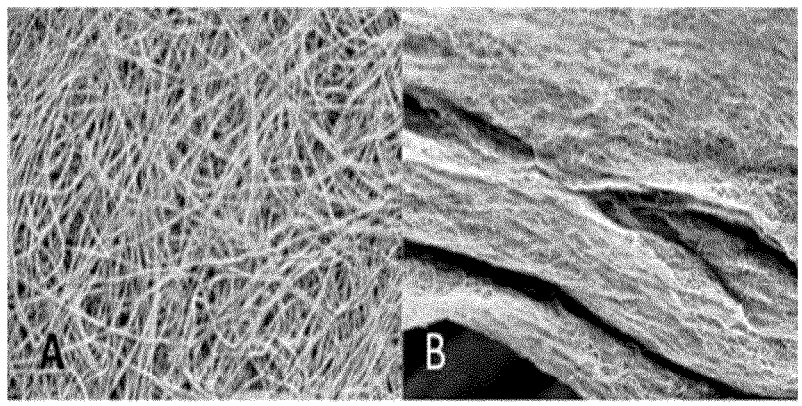
FIG. 4. Electrospun (A) and plastic compressed (B) collagen fibres resembling dermal ECM (extracellular matrix).

The inventors have been able to reproduce the morphology of the meshes found in decellularized dermis by eletrospinning and plastic compression of porcine collagen alone or with other polymers (FIGS. 4A and B). However, to optimize the components of the dermal scaffold not only to support dermal fibroblasts but to allow for blood vessel in-growth, a soft fibrin hydrogel pre-seeded with EPCs may be incorporated to allow very rapid angiogenesis and allow for anatomosis formation, which is critical to successful grafting.

Although compressed fibrous meshes can be used as skin substitutes, a smooth substrate is more desirable for a smooth skin epidermis. The mesh may therefore be arranged within a hydrogel. Because of the cell friendly chemistry of the present hydrogel it is possible to incorporate cells (e.g. autologously harvested and expanded) into the fibrous mesh-hydrogel construction.

A cornea implant may have a thickness of 150-500 μm, such as 250-350 μm. The implant may be prepared by placing the hydrogel or the solutions forming the gel between two plates or molds having the desired thickness as a distance between the plates/molds. UV (for example 365 nm wavelength) may be applied for 5 to 20 minutes, such as 10-15 minutes.

CMP hydrogels have comparable mechanical properties to recombinant human collagen and are sufficiently robust for grafting as corneal implants, as shown in grafts into mini-pigs. Example 3 discloses some properties of some CMP hydrogels.

The hydrogels according to the present invention may also be used in lab-on-a-chip systems, microscopy and microarray substrates, cell and tissue culture dishes, microwell plates, microfluidic and sampling, separation, purification, analytical tools. In this type of applications, the hydrogel can be used as an optimal support/environment for cell growth, proliferation, differentiation, tissue formation. Also, the hydrogel can be employed as a technical material for production of any kind of component for the above devices. The hydrogel can be used in the device as produced or it can be post-fabricated in order to obtain a specific shape, morphology, topography, stiffness, surface chemical, biochemical or physical properties, etc.

EXAMPLES

Example 1—Hydrogel of MAC and PEG-SH

Figure 5:
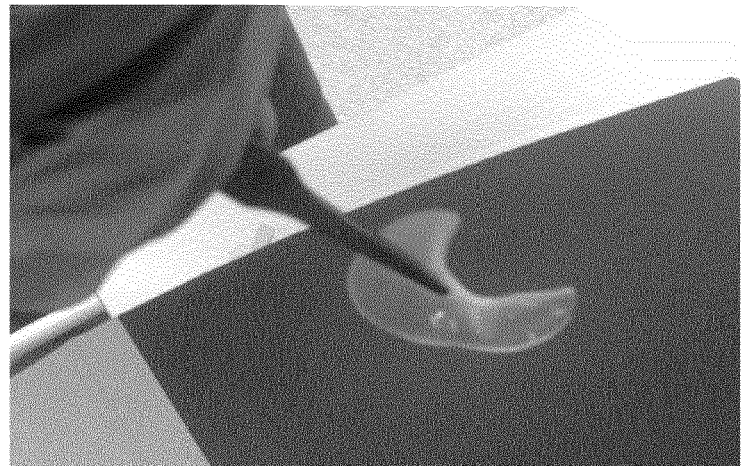
FIG. 5. Stiff hydrogel of MAC/4-arm PEG-thiol.

A hydrogel from the Michael addition reaction was prepared by mixing 0.5 mL of 10 wt % MAC with a 4-arm PEG thiol using a three way syringe system. The PEG thiol was dissolved in water and added to get the overall concentration of methacrylated collagen of 5%. The solution from the syringe was casted between two glass slides/molds with spacers of desired thickness and stored under humid conditions overnight. A stiff hydrogel was obtained, as shown in FIG. 5. This result confirms the proof-of-concept that a stiff hydrogel can be prepared by the overnight reaction of MAC with a 4 arm PEG thiol. The absence of UV light and by-products makes this hydrogel promising for corneal application. Such features make this hydrogel suitable for encapsulation and delivery of stromal stem cells in cases of HSV conditions, when the patient lacks the pool of the stem cells, thus making conventional regenerative approaches impractical.

Example 2—Methacrylation of Collagen 0.5% collagen solution in 1×PBS was prepared (pH 6.5-6.7). The pH was raised to 10 using NaOH at −4° C. Methacrylic anhydride (10:1 molar ratio w.r.t. amine groups in collagen) was added drop wise to collagen solution in 3 batches and the solution was stirred vigorously for 4 hours. The reaction mixture was dialyzed for 4 days against distilled water at room temperature.

Figure 6:
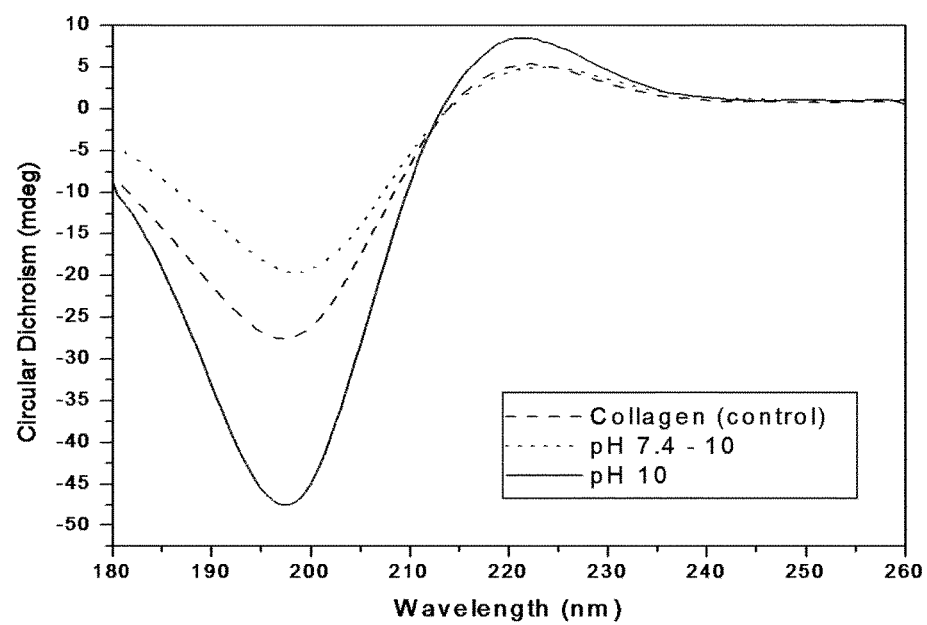
FIG. 6. Circular dichronism of MAC.
Figure 7:
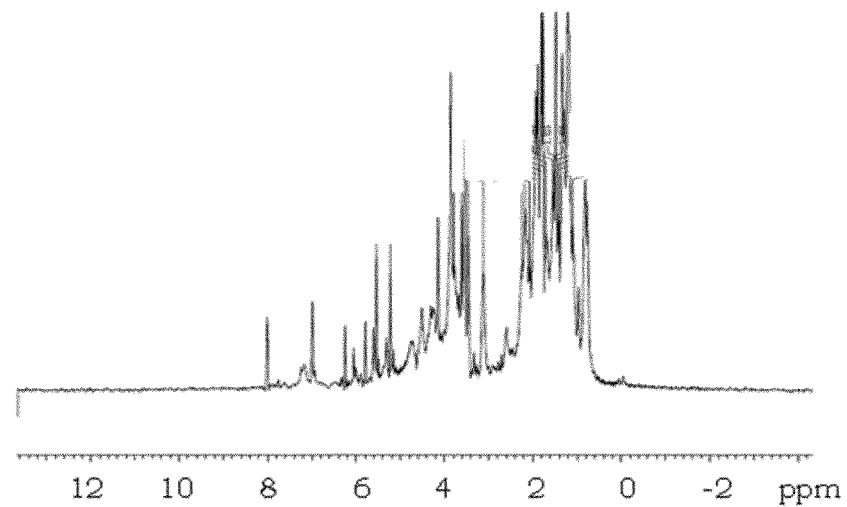
FIG. 7. NMR of MAC. New peaks between 5-6 ppm are characteristic for methacryalation of collagen.

The results from circular dichroism and NMR are found in FIGS. 6 and 7.

The circular dichroism spectrum of MAC at 1% by weight concentration in Milli-Q water, at room temperature, showed maximum at 225 nm and a minimum near 200 nm at pH 7.4 and pH 10 which is indicative of collagen triple helices. The triple helical propensity is higher at high pH.

HNMR spectra of MAC at 1% by weight concentration in $D_2O$, at room temperature showed two new peaks between 5-6 ppm, characteristic for two acrylic protons of methacrylic functionality.

The inventors found that transparency was achieved by varying the pH of methacrylated collagen (MAC) in water. MAC was transparent if the pH was either less than 5 or above 10. This is something not reported before.

Example 3—Formation of Hydrogel with MAC and Acrylate Monomers

Mixing of MA-Collagen with Acrylate Monomers to Form Multicomponent Gel 0.3 mL (300 μL) of 5% MA-collagen (MAC) solution was taken in the 3 way syringe system and 300 μL of polyethylene glycol-diacrylate (PEGDA), PEG methacrylate (PEGMA), hydroxyethyl methacrylate (HEMA), polyethylene glycol methyl ether methacrylate (PEGMEM) containing 2% (w.r.t collagen) Irgacure 2959 was added to the syringe and mixed well. The solution from the syringe was casted between two glass slides/molds with spacers of desired thickness and exposed to UV 365 nm wavelength for 10 to 15 min.

TABLE 1

Experimental set up.

| MAC | Acrylate monomer | Ratio (mol) |
|---|---|---|
| 300 μL | 300 μL | 1:1 |

Mixing of MA-Collagen with Multiple Acrylate Monomers to Form Multicomponent Gel 300 μL of 5% MA-collagen was mixed with two different acrylate monomers e.g. (HEMA+PEGDA) with 2% (w.r.t collagen) Irgacure 2959 and mixed well. The solution from the syringe was casted between two glass slides/molds with spacers od desired thickness and exposed to UV 365 nm wavelength for 10 to 15 min.

TABLE 2

Experimental set up.

| MAC | HEMA | PEGDA | Ratio |
|---|---|---|---|
| 300 μL | 150 μL | 150 μL | 1:0.5:0.5 |

Figure 8:
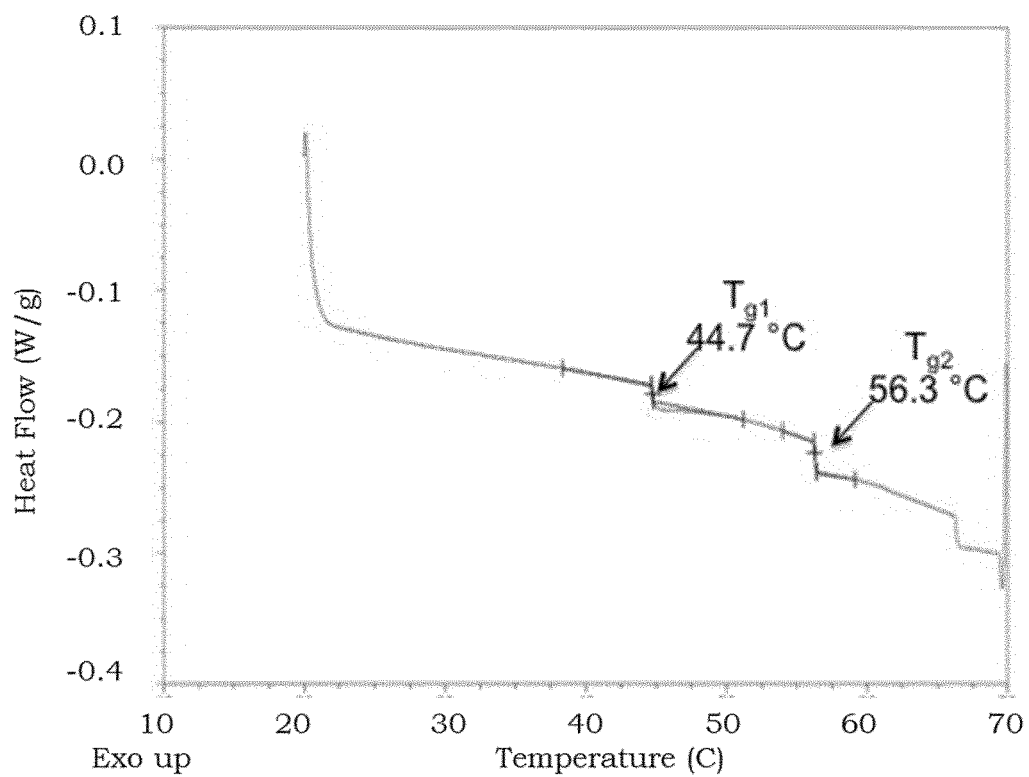
FIG. 8. DSC curve from MAC-HEMA hydrogel.

FIG. 8 shows the DSC curve of the MAC-HEMA hydrogel. It shows that the hydrogel comprises at least two polymer networks with $T_{g1}$ and $T_{g2}$ of 44.7 and 56.3° C., respectively. A third step is visible in the curve, but further studies are needed to confirm the presence of a three-polymer hydrogel.

Example 3—Preparation of CMP Hydrogel

T-piece mixing system was used to make hydrogels with CMP, which was previously described. For making the hydrogel 500 mg of 12% (w/w) CMP was mixed with 300 μl of water. Calculated volumes of NHS and then EDC were added to the syringe mixing system. Depending on the molar equivalent ratio of EDC to amine of CMP, 3 different types of hydrogel were made; $CMP-NH_2:EDC=1:0.5$, $CMP-NH_2:EDC=1:1$ and $CMP-NH_2:EDC=1:2$. The molar ratio of EDC:NHS was 1:1. The stock solution concentrations of EDC and NHS were adjusted in such a way that in all different types of hydrogels, dilution factor of CMP remained same. All addition followed by thorough mixing. Table 3 and 4 discloses some results and properties of the obtained hydrogels. Circular dichroism revealed triple helical formation.

TABLE 3

Mechanical properties of CMP hydrogels.

| Formulation CMP:EDC/NHS ratio | Tensile strength/ max Load (kPa) | Elongation at Break (%) | Young's Modulus (mPa) |
|---|---|---|---|
| 1:0.5 | 1.47 ± 1.2 | 67.10 ± 37.20 | 0.22 ± 0.05 |
| 1:1 | 1.79 ± 0.5 | 64.02 ± 8.09 | 0.21 ± 0.08 |
| 1:2 | 0.99 ± 0.3 | 30.04 ± 7.42 | 0.26 ± 0.04 |

TABLE 4

Water content of CMP hydrogels.

| Formulation | Initial Wt | 1 h drying | Water Content (%) | 24 h drying | Water Content |
|---|---|---|---|---|---|
| CMP 1:1 | 45.9 | 20.6 | 55% | 3.2 | 93% |
| CMP 1:1 | 39.4 | 16.6 | 58% | 3 | 92% |
| CMP 1:2 | 49.3 | 23.5 | 52% | 4.9 | 90% |
| CMP 1:2 | 48.3 | 22.2 | 54% | 4.3 | 91% |

Example 4—In Vivo Study of CMP Hydrogel

Figure 10:
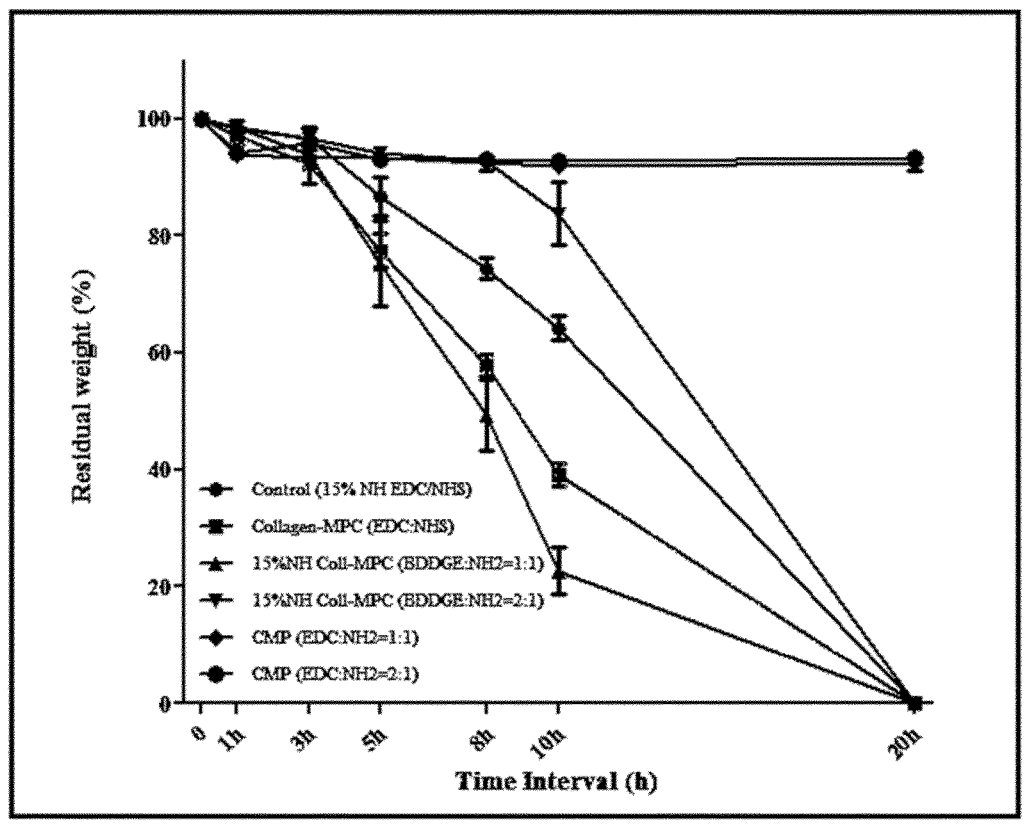
FIG. 10. Graph showing collagenase digestion of CMP compared to other collagen-based hydrogels.

The CMP-EDC 1:2 hydrogel was tested in vivo in a pig. Cornea shaped implants were implanted into the eyes of three pigs and regular analysis were conducted. As positive control collagen based hydrogel was used and the results from the CMP hydrogel have so far been as good as for the collagen. CMP hydrogels integrates into the host tissue and discloses epithelial regeneration after 2 weeks already. After 3 months the sensitivity of the eye was restored together with the tear formation function. After 9 months nerves were regenerated. The stability of the hydrogel is seen in FIG. 10.

The invention claimed is:

1. A hydrogel of a cross-linked polymer network comprising:
   at least one first polymer including a collagen mimetic peptide (CMP) having amine groups, the CMP including methacrylate or acrylate functional groups along its triple helical chain and connected to a template polymer having at least two arms; and
   at least one second polymer including a synthetic polymer or a natural polymer having at least two functional groups selected from thiol, acrylate and methacrylate,
   wherein the first and the second polymers are intermolecularly cross-linked via said functional groups,
   wherein the hydrogel has a light transmission of at least 80% of light in a range of 400-700 nm, and
   wherein a total concentration of polymers in the hydrogel is at least 2 weight %.

2. The hydrogel according to claim 1, wherein the template polymer is selected from multiarm polyvinyl chloride, spider silk, succinylated poly(N-isoacrylamide), or a terpolymer of poly(N-isopropylacrylamide-coacrylic acid-coacryloxysuccinimide (PNiPAAm-coAAc-coASI).

3. The hydrogel according to claim 1, wherein the second polymer is a polymer selected from functionalized polyethylene glycol (PEG), polyvinyl alcohol (PVA), polyethylene glycol-diacrylate (PEGDA), PEG methacrylate (PEGMA), poly(hydroxyethyl methacrylate) (pHEMA), polyethylene glycol methyl ether methacrylate (PEGMEM), poly(pentaerythritol triacrylate) or poly(N-isopropylacryl amide) (PNIPAAm).

4. The hydrogel according to claim 1, wherein the second polymer has three or more arms.

5. The hydrogel according to claim 1, wherein the hydrogel is cross-linked photochemically or via Michael addition reaction with 1-Ethyl-3-(3-dimethylaminopropyl)carbodiimide (EDC) and N-Hydroxysuccinimide (NHS).

6. The hydrogel according to claim 1, wherein the light transmission is at least 90%.

7. A three dimensional scaffold comprising cells and the hydrogel according to claim 1.

8. The scaffold according to claim 7, wherein the cells are stem cells.

9. An implant comprising the hydrogel according to claim 1.

10. The implant according to claim 9, wherein the implant is a cornea implant.

11. A method comprising:
    replacing a damaged or malfunctioning cornea with the implant according to claim 10.

12. A method of preparing the hydrogel according to claim 1, the method comprising:
    providing a first aqueous solution of a first polymer including a collagen mimetic peptide (CMP) having amine groups, the CMP including methacrylate or acrylate functional groups and connected to a template polymer having at least two arms;
    providing a second aqueous solution of a second polymer including a synthetic polymer having at least two functional groups selected from thiol, acrylate and methacrylate, or synthetic monomers having thiol, acrylate and/or methacrylate functional groups;
    mixing the first polymer and the second polymer or synthetic monomers to cross-link the functional groups of the first polymer and the second polymer or synthetic monomers and obtain a mixture having a total polymer concentration of at least 2 weight %; and
    applying UV radiation to the mixture.

13. The method according to claim 12, wherein
    the first polymer is methacrylated CMP, and
    a pH of the first aqueous solution is less than 5 or more than 10.

14. The method according to claim 12, wherein a total concentration of polymers in the mixture is at least 12 weight %.

15. The method according to claim 12, wherein the mixing is performed using a syringe mixing system.

16. A method of using the hydrogel according to claim 1 in at least one of lab-on-a-chip systems, microscopy and microarray substrates, cell and tissue culture dishes, microwell plates, microfluidic or sampling, separation, purification, and analytical tools, wherein the hydrogel is configured to support cell growth, proliferation, differentiation, and tissue formation.

17. An injectable composition comprising:
    a first aqueous solution including collagen mimetic peptide (CMP) having amine groups, the CMP including methacrylate or acrylate functional groups along its triple helical chain and connected to a template polymer having at least two arms; and
    a second aqueous solution including a synthetic polymer having two or more functional groups selected from thiol, acrylate and/or methacrylate,
    wherein a polymer concentration in each of the first and second aqueous solutions is not more than 3 weight %,
    wherein the first and second aqueous solutions form a gel when mixed, and
    wherein,
        the composition is in a syringe having two separate compartments, the first aqueous solution is in a first compartment of the two separate compartments, and the second aqueous solution is in a second compartment of the two separate compartments.

18. The composition according to claim 17, wherein the composition further comprises cells, growth factors, or cell nutrients.

* * * * *